(12) United States Patent
Biedermann et al.

(10) Patent No.: US 6,471,705 B1
(45) Date of Patent: Oct. 29, 2002

(54) BONE SCREW

(76) Inventors: Lutz Biedermann, Am Schäfersteig 8, 78048 VS-Villingen (DE); Jürgen Harms, Im Zeitvogel 2, 76227 Karlsruhe (DE)

(*) Notice: Subject to any disclaimer, the term of this patent is extended or adjusted under 35 U.S.C. 154(b) by 0 days.

(21) Appl. No.: 09/806,787

(22) PCT Filed: Jun. 27, 2000

(86) PCT No.: PCT/EP00/05966

§ 371 (c)(1),
(2), (4) Date: Apr. 2, 2001

(87) PCT Pub. No.: WO01/08574

PCT Pub. Date: Feb. 8, 2001

(30) Foreign Application Priority Data

Aug. 2, 1999 (DE) .......................... 199 36 286

(51) Int. Cl.⁷ .............................. A61B 17/70
(52) U.S. Cl. .......................... 606/61; 606/72
(58) Field of Search ............... 606/60, 61, 72, 606/73

(56) References Cited

U.S. PATENT DOCUMENTS 5,443,467 A * 8/1995 Harms .................. 606/61
5,474,555 A * 12/1995 Puno et al. ............ 606/73
5,624,442 A * 4/1997 Byrd ..................... 606/65
5,672,176 A * 9/1997 Biedermann et al. ..... 606/61
5,681,319 A * 10/1997 Biedermann et al. .... 606/104

FOREIGN PATENT DOCUMENTS

CH    WO9832286 A  *  7/1998  .......... 606/61
FR    2697992 A    *  5/1994  .......... 606/61

* cited by examiner

Primary Examiner—Nicholas D. Lucchesi
Assistant Examiner—Michael B. Priddy
(74) Attorney, Agent, or Firm—George W. Neuner; Edwards & Angell, LLP

(57) ABSTRACT

There is provided a bone screw known per se, having a threaded portion (2) and a reception part (5) for receiving a rod (29) to be connected to the bone screw. The securing and locking action of the connection between the bone screw and the rod is provided by an exterior nut (13). To provide for the required strength and durability of the connection, the exterior nut (13) comprises an inside sleeve-shaped element (17) having a predetermined inner dimension and an outer diameter which is almost equal to or slightly less than the diameter of the bore (8), and a pressure element (22) arranged therein. The pressure element (22) comprises a first section (26) at its end facing the bottom of the bore hole (8). The outer dimension of the first section is greater than the predetermined inner dimension and the first section causes the element (17) to be expanded when pressure is exerted on the rod (29) to be received.

10 Claims, 3 Drawing Sheets

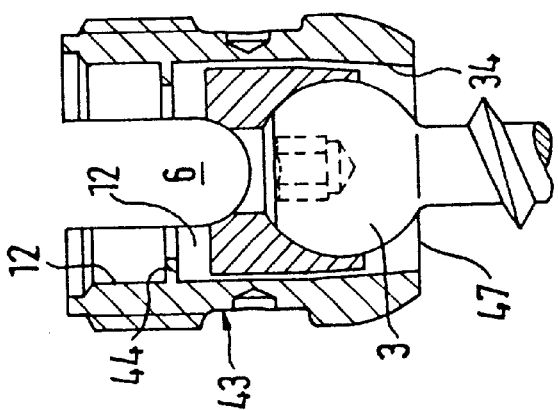
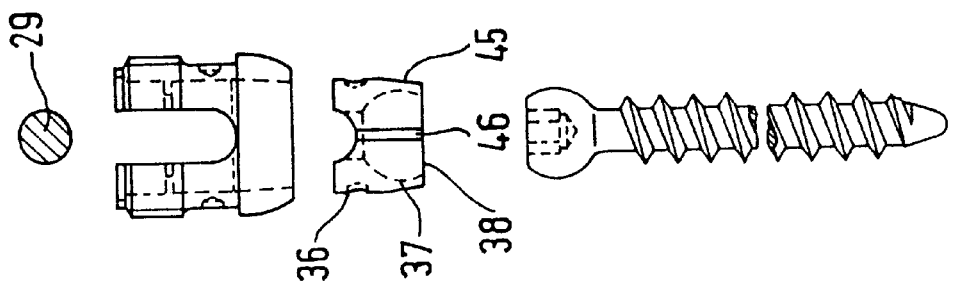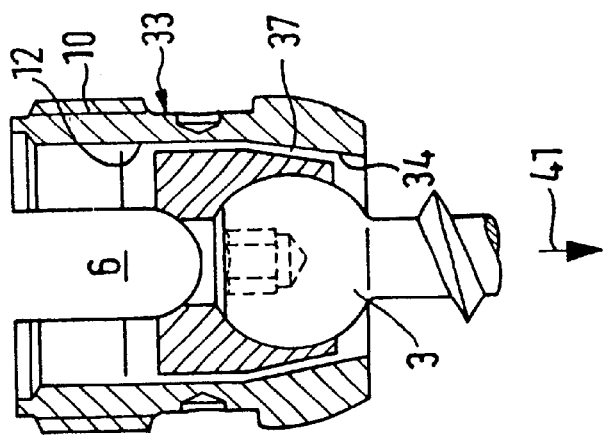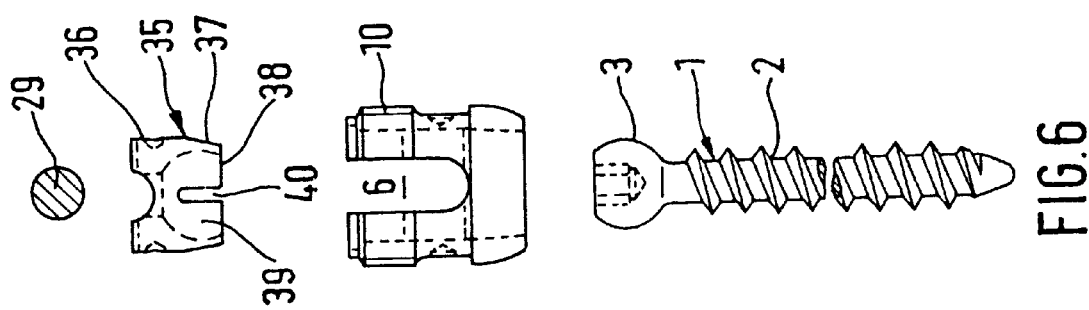

BONE SCREW

The present invention relates to a bone screw according to the pre-characterizing portion of claim 1.

A bone screw of this type is known from EP 0 614 649 A where a safety nut to be screwed into an open bore is provided for perfectly locking the connection of the rod and the bone screw.

It is an object of the present invention to provide a bone screw of the above type which does not require such an interior nut.

This object is achieved by a bone screw as characterized in claim 1.

Further embodiments of the present invention are characterized in the dependent claims.

The invention will be better understood from the following description and figures of a preferred embodiment which is presented for illustrative purposes only and is not to be construed as limiting the scope of the present invention.

FIG. 6 is a lateral exploded view corresponding to FIG. 1, of a second embodiment of the bone screw;

FIG. 7 is a sectional view across the bone screw of the second embodiment;

FIG. 8 is a lateral view corresponding to FIG. 1, of a third embodiment of the bone screw; and FIG. 9 is a sectional view across the third embodiment.

Figures 1, 2:
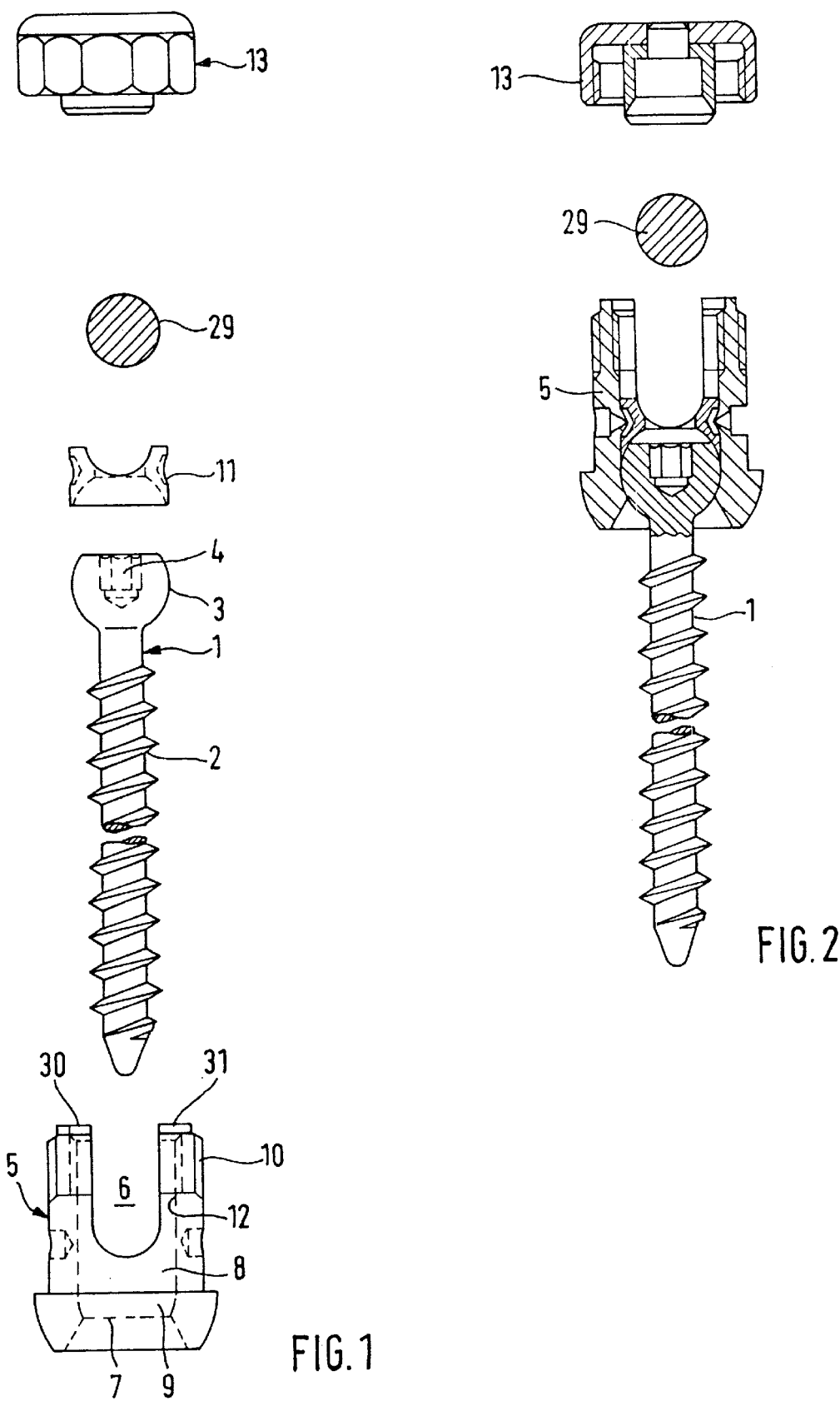
FIG. 1 is an exploded lateral view of a first embodiment of a bone screw.
FIG. 2 is a sectional view across the bone screw.

The bone screw according to the embodiment shown in FIGS. 1 and 2 comprises the actual screw element 1 having a threaded portion 2 and a head 3. The head is formed as a spherical segment portion adjacent to the threaded portion. In coaxial relationship with the thread axis and on the end opposite to the threaded portion 2, the head comprises a recess 4 to be engaged with an Allen key (hexagon socket screw key).

In addition, the bone screw comprises a cylindrically shaped reception part 5. At one of its ends, it comprises an axissymmetrical bore 7 having a diameter greater than that of the threaded portion 2 and less than that of the head 3. The reception part 5 further comprises a coaxial second bore hole 8 being open at the end opposite to the first bore hole 7 and having a diameter large enough for the screw element 1 to be guidable through the open end with its threaded portion 2 and all the way to the bottom of the second bore hole with its head 3. Between the first and the second bore hole, a small coaxial portion 9 is provided in immediate adjacent relationship with the first bore hole and having a spherical shape toward the open region, with its radius being substantially equal to the radius of the spherical segment portion of the head 3. In addition, the reception part 5 comprises a U-shaped recess 6 arranged symmetrically with respect to the center of the part, having a bottom facing the first bore hole 7 and with its pair of lateral legs 30, 31 reaching to the open end facing away from the first bore hole 7. An external thread 11 is provided at the free end of the legs of the U-shaped recess.

At the side located at the free end of the head 3, there is located a pressure disk 11 formed in such a way that it comprises a spherically lowered region at its side facing the head 3, the radius of the spherically lowered region being substantially equal to the radius of the spherical segment portion. The outer diameter of the pressure disk 11 is selected such that it may perform a gliding motion into the cylinder portion 12 of the second bore 8, i.e. it may be shifted within the cylinder portion towards the head. The pressure disk comprises a coaxial bore permitting access to the recess 4.

The bone screw further comprises an exterior nut 13 which will be explained in more detail referring in particular to FIGS. 3 to 5. The exterior nut is formed as a cap nut and comprises a conventional lateral threaded portion 14 constituting the actual nut and a cover portion 15 extending from the threaded portion at its outer side facing away from the threaded portion. Although the cover portion is formed as in a conventional cap nut, it further comprises a concentric bore 16 having a first diameter. Also, there is provided a sleeve 17 comprising a hollow cylinder shaped jacket 18 and a bottom 19 at its side facing the cover portion 15. In the bottom 19 a concentric bore 20 having a second diameter is provided. The second diameter is equal to the first diameter of the bore 16 or slightly greater than it. As can be best seen from FIG. 3, the hollow cylindrical jacket 18 comprises an edge 21 at its inner side at its free end facing away from the bottom 19, which edge is bevelled towards the outside such that it has the shape of a truncated cone with the angle of inclination of the bevel with respect to the inner cylinder wall being about 30° to 60° and preferably about 40°. The outer diameter of the cylindrical sleeve 17 is almost identical to the diameter of the second bore 8 and smaller than it by an amount just enabling the sleeve to be inserted without friction into the second bore 8.

In addition, a pressure element 22 is provided which comprises a second cylinder shaped portion 23. The outer diameter of the cylinder is substantially equal to the inner diameter of the cylinder jacket 18. It is dimensioned such that the pressure element is held in it by frictional force due to the insertion of the second portion into the inside of the jacket 18. As can be best seen from FIG. 4, the height of the second portion in the axial direction is slightly less than the corresponding length of the cylinder portion 24 of the jacket 18.

Preferably, the difference ranges from 0.25 to 0.5 millimeters. At the side facing the cover portion, the second section is formed as a planar shape and comprises a concentrically arranged pin-shaped projection 25. The diameter of this projection substantially corresponds to the diameter of the bore 16 and it is dimensioned such that the pin is held in the bore 16 due to frictional force. At the side facing away from the cover portion 15, the second section 23 comprises a first section 26 extending therefrom. It is formed as a truncated cone shape such that the small inner diameter corresponds to the diameter of the second section 23 and that the diameter of the surface facing away from the second section is equal to the diameter of the portion of the bevelled edge 21 resting on it. Preferably, the angle of the envelope of the cone is equal to the angle of the inner edge 21.

Figure 4:
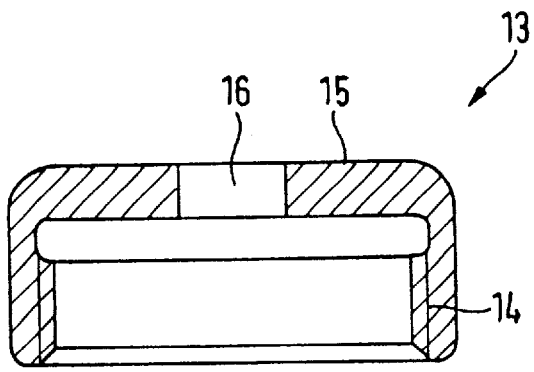
FIG. 4 represents the exterior nut in an assembled condition before acting on the rod.
Figure 4:
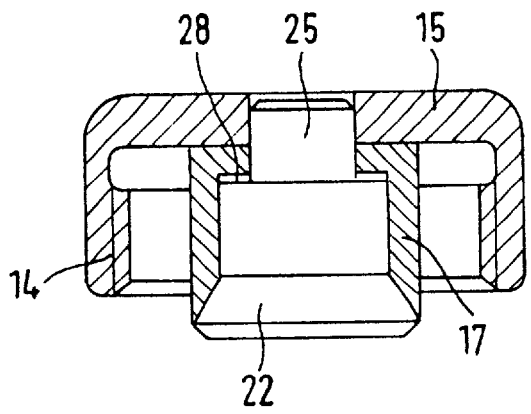
Figure 4:
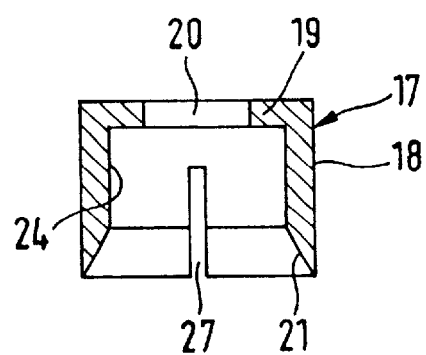
Figure 5:
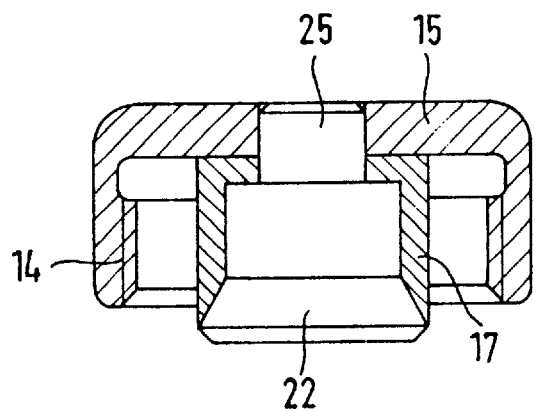
FIG. 5 is the same representation after acting on the rod.

Thus, in the preassembled condition shown in FIG. 4, a gap-shaped spacing 28 is established between the bottom 19 of the sleeve 17 and the bottom surface 32 facing it.

Figure 3:
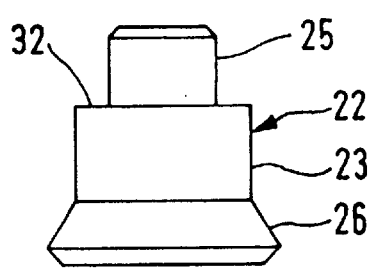
FIG. 3 is an enlarged-scale exploded view, partially in section, of an exterior nut to be used with the bone screw.

As can be best seen from FIG. 3, at its edge facing away from its cover portion, the sleeve 17 comprises a slit 27 extending in a direction parallel to the axis of symmetry of the sleeve and enabling the free edge of the sleeve to be expanded.

In use, the screw element 1, the reception part 5 and the pressure disk are first assembled in the known manner, as can be best seen from FIG. 2. Next, the rod 29 to be connected with the bone screw is inserted. The exterior nut is preassembled in the condition shown in FIG. 4, i.e. the pressure element 22 is inserted in the sleeve 17 and thus connected to the cover portion 15 together with the sleeve by the projection 25 being urged into the bore hole 16. The nut preassembled in this way is now screwed onto the external thread of the reception part 5. In this situation, on the one hand, the rod 29 rests on the pressure disk 11. On the other hand, it is exposed to pressure by the pressure element 22 being screwed on and contacting the rod once the exterior nut 13 has almost reached its end position. As the screwing of the exterior nut into the desired end position is continued, the pressure element 22 is urged to the very bottom of the sleeve 17 for the reason illustrated in FIG. 5. As a simultaneous result, the first section 26 will act on the free end of the sleeve 17 such that the sleeve or its free end will be urged toward the outside in the manner shown in FIG. 5. Thus, the jacket 18 is enabled to again exert a force with its outer surface onto the free legs 30, 31 in the region of the exterior thread 10 such that these free legs 30, 31 will again urge the threaded portion 10 into the section 14 comprising the interior thread. This will cause a locking action preventing unintentional loosening of the exterior nut 13.

In the embodiment described above, a so-called polyaxial screw is dealt with where the screw element 1 and the reception part 5 can be moved in angular relationship relative to each other. In a modified embodiment, the screw element 1 and a reception part receiving the rod 29 are made in one piece, e.g. such that the reception part 5, the head 3 and the pressure disk 11 are made in one piece in the manner shown in FIG. 2. In this case, the shape of the exterior nut 13 will be identical to the one described above. In use, the locking of the exterior nut is effected by the force from rod 29 acting on the pressure element 22 in the manner described above such that the same locking is achieved.

The second embodiment shown in FIGS. 6 and 7 differs from the first embodiment by the formation of the reception part. As in the first embodiment, the second bore comprises a cylinder portion 12. Instead of the first bore 7 and the spherical segment 9, a portion having a portion 34 conically tapering away from the second portion is provided. Instead of the pressure element 11, a pressure element 35 is provided which comprises a cylindrical portion 36 and adjacent thereto a conical segment shaped portion 37. On the end surface 38 surrounded by the conical segment shaped portion 37, the element comprises a conical segment shaped recess 39 having a diameter approximately equal to or equal to the outer diameter of the head 3. As shown in FIG. 6, the wall of the portion 37 comprises a slit 40 extending from the end surface 38 in an axial direction. The outer dimension of the conical segment shaped portion 37 is selected in such a manner that the diameter at the portion adjacent to the cylindrical portion 36 is greater than the diameter of the portion 34 at its free and open end. At the same time, the inclination of the conical segment shaped portion 37 is selected to be substantially equal to the inclination of the portion 34. Furthermore, the diameter of the conical segment shaped portion 37 at its side adjacent to the cylindrical portion 36 is equal to the diameter of the cylindrical portion 36 and less than or almost equal to the inner diameter of the cylinder portion 12.

In use, starting from the opening formed by the free end of the portion 34, the screw element 1 is pushed through the opening 34 and the cylinder portion 12 and, starting from the end surface 38, is urged into the pressure element 35 into the recess 39. Thereafter, the screw element together with the pressure element thus attached is moved into the position shown in FIG. 7 and then in the direction of arrow 41 far enough for the conical segment shaped portion 37 to gently abut portion 34. All the features and in particular the external thread 10 of the outer shape of the reception part 33 coincide with the first embodiment. The exterior nut which can be used with this embodiment is identical to the embodiment shown in FIGS. 3 and 4.

In use, as in the first embodiment, the rod 29 is put into the U-shaped recess 6 and secured by the exterior nut 13. The dimensions of the exterior nut relative to the diameter of the cylinder portion 12 correspond to the first embodiment.

In the third embodiment shown in FIGS. 8 and 9, the reception part 43 is identical to the reception part 33 except for one feature. According to this feature, an annular segment shaped stop 44 is provided in the cylinder portion 12 a predetermined distance from the free end of the cylinder portion.

A pressure element 45 coincides in all its features with the pressure element 35 except for one feature. Instead of the non-continuous slit 40, a slit 46 is provided which extends all the way from the end adjacent to the end surface 38 to the opposite end. Other than that, the relative dimensions of the cylindrical portion and the conical segment shaped portion 37 coincide with the inner dimensions of the cylinder portion 12 and the portion 34.

The slit 46 is selected to be wide enough such that the pressure element 45 can be compressed in peripheral direction far enough for it to be inserted from the bottom side 47 of the portion 34 into the cylinder portion 12 and all the way to the stop 44. The outer diameter of the conical segment shaped portion 37 has been selected at its free end in such a manner that in its stop position, it is smaller by as much as the inner diameter of the adjacent wall, that an expansion of the conical segment shaped portion 37 becomes possible, that the head 3 is inserted in the bottom side 47 and can be urged into the pressure element 45 and is held by the latter in the same fashion as in the second embodiment. After urging the head 3 into the pressure element, the pressure element 45 will have the same dimensions relative to the inner dimensions of the reception part 43 as in the second embodiment.

In use, the rod 29 is put into the U-shaped recess 6 as in the previous embodiments. Next, the exterior nut is screwed on as in the previous embodiments, thus achieving a locking action between the reception part 43 and the screw element 1.

What is claimed is:
1. A bone screw comprising:
   a screw part having a head and a threaded portion;
   a head-side cylindrical reception part for receiving a rod to be connected with the screw part;
   said reception part comprising an open bore hole and a U-shaped cross section having two free legs provided with an exterior thread; and
   an exterior nut which can be screwed onto the exterior thread,
   wherein the exterior nut comprises an inside sleeve-shaped element having a predetermined inner dimension and an outer diameter which is almost equal to or slightly less than the diameter of the bore, and a pressure element arranged therein,
   said pressure element comprising an end facing the bottom of said bore and a first section at said end, the outer dimension of said first section being greater than said predetermined inner dimension and said first section causing said sleeve-shaped element to be expanded when pressure is exerted on the rod to be received.

2. The bone screw as claimed in claim 1, wherein said exterior nut is formed as a cap nut having a cover portion and a lateral threaded portion provided at an outer edge thereof, said sleeve-shaped element comprising a cylindrical portion of predetermined length extending in an axial direction, and said pressure element comprising a second section having an axial length which is less than the length of said cylindrical portion.

3. The bone screw as claimed in claim 2, wherein said sleeve-shaped element includes a free end facing away from the cover portion and, at said free end, the sleeve-shaped element comprises a wall portion being convex outwardly, which is abutted by the first section of said pressure element.

4. The bone screw as claimed in claim 3, wherein said first section is formed in a truncated cone shape with the base being located on a side facing the bottom of the bore.

5. The bone screw as claimed in claim 4, wherein said sleeve-shaped element and said pressure element on the one hand and said cover portion on the other hand are connected with each other.

6. The bone screw as claimed in claim 5, wherein said cover portion comprises a concentric bore, and said pressure element comprises a protruding concentric projection on a side facing the cover portion, and wherein the projection is held in the bore.

7. The bore screw as claimed in claim 6, wherein said sleeve-shaped element includes a side facing the cover portion, on which said sleeve-shaped element comprises a bottom having a concentric bore, and wherein said projection is provided at an end of said pressure element facing said bottom.

8. The bone screw as claimed in claim 4, wherein said sleeve-shaped element has a free end that comprises an inner truncated cone shaped section having an inclination which is substantially equal to the inclination of said first section.

9. The bone screw as claimed in claim 3, wherein said sleeve-shaped element includes at least one slit starting from the free end.

10. The bone screw as claimed in claim 2, wherein said pressure element protrudes from the lateral threaded portion in an axial direction.

* * * * *